United States Patent
Guyon et al.

(10) Patent No.: US 12,427,289 B2
(45) Date of Patent: Sep. 30, 2025

(54) BALLOON CATHETER WITH ENHANCED CHARACTERISTICS

(71) Applicant: MicroVention, Inc., Aliso Viejo, CA (US)

(72) Inventors: Roland Guyon, Cowan Heights, CA (US); Joseph Gulachenski, Trabuco Canyon, CA (US); Binh Nguyen, Lake Forest, CA (US); Russel Corvese, Aliso Viejo, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 546 days.

(21) Appl. No.: 17/096,813

(22) Filed: Nov. 12, 2020

(65) Prior Publication Data

US 2021/0138205 A1  May 13, 2021

Related U.S. Application Data

(60) Provisional application No. 62/934,423, filed on Nov. 12, 2019.

(51) Int. Cl.
A61M 25/10 (2013.01)

(52) U.S. Cl.
CPC ..... *A61M 25/10* (2013.01); *A61M 2025/1061* (2013.01); *A61M 2025/1077* (2013.01)

(58) Field of Classification Search
CPC .......... A61M 25/10; A61M 2025/1061; A61M 2025/1077; A61M 25/1006; A61M 25/1018; A61M 2025/109
See application file for complete search history.

(56) References Cited

U.S. PATENT DOCUMENTS

| | | | |
|---|---|---|---|
| 4,259,960 A | | 4/1981 | Taylor |
| 5,256,145 A | * | 10/1993 | Atkinson ............ A61M 25/104 604/103 |
| 5,378,237 A | * | 1/1995 | Boussignac ......... A61M 25/104 604/103.01 |
| 5,951,513 A | | 9/1999 | Miraki |
| 6,221,063 B1 | | 4/2001 | Harra et al. |
| 6,613,066 B1 | * | 9/2003 | Fukaya ............. A61M 25/1034 606/198 |
| 2003/0212360 A1 | | 11/2003 | Shkolnik |
| 2008/0097300 A1 | | 4/2008 | Eskaros et al. |
| 2009/0281490 A1 | | 11/2009 | McAuley et al. |

(Continued)

FOREIGN PATENT DOCUMENTS

| | | |
|---|---|---|
| JP | 2000-507871 A | 6/2000 |
| JP | 2019-520882 A | 7/2019 |

(Continued)

OTHER PUBLICATIONS

WIPO, U.S. International Search Authority, International Search Report and Written Opinion mailed Mar. 18, 2021 in International Patent Application No. PCT/US2020/060296, 15 pages.

(Continued)

*Primary Examiner* — Thomas McEvoy
(74) *Attorney, Agent, or Firm* — Inskeep IP Group, Inc.

(57) ABSTRACT

A balloon catheter is described with features to reduce balloon stickiness thereby ensuring a more even inflation profile. In some embodiments, a balloon guide catheter is described which includes a conduit or passage for additional catheters or devices.

20 Claims, 9 Drawing Sheets

(56) References Cited

U.S. PATENT DOCUMENTS

| | | | |
|---|---|---|---|
| 2010/0313895 A1* | 12/2010 | O'Neil | A61M 16/0427 128/207.15 |
| 2012/0253447 A1 | 10/2012 | Hayasaka et al. | |
| 2014/0121596 A1 | 5/2014 | Bo | |
| 2016/0045719 A1 | 2/2016 | Ha et al. | |
| 2016/0263355 A1 | 9/2016 | Katsurada et al. | |
| 2017/0348514 A1 | 12/2017 | Guyon et al. | |
| 2024/0198060 A1 | 6/2024 | Casey et al. | |

FOREIGN PATENT DOCUMENTS

| | | |
|---|---|---|
| WO | WO 1998/030269 A2 | 7/1998 |
| WO | WO 1999/021604 A3 | 5/1999 |
| WO | WO2014/209735 A1 | 12/2014 |
| WO | WO 2017/210092 A1 | 12/2017 |

OTHER PUBLICATIONS

European Patent Office, Extended European Search Report dated Jan. 3, 2024 in European Patent Application No. 20887227.5-1122, 8 pages.

China National Intellectual Property Administration, Office Action issued Oct. 25, 2023 in Chinese Patent Application No. 202080090886.7 filed Nov. 12, 2020 (with English translation), 12 pages.

Japan Patent Office, Office Action dated Oct. 29, 2024 with English translation in Japanese Patent Application No. 2022-527153, 5 pages.

* cited by examiner

BALLOON CATHETER WITH ENHANCED CHARACTERISTICS

RELATED APPLICATIONS

This application claims priority to U.S. Provisional Application Ser. No. 62/934,423 filed Nov. 12, 2019 entitled Non-stick Balloon Catheter, which is hereby incorporated herein by reference in its entirety.

BACKGROUND

Balloon catheters can be used for various procedures in the vasculature, including flow arrest, flow reversal, occlusion, acting as a scaffold for subsequently delivered medical devices, and as part of an aspiration or clot retrieval procedure to arrest blood flow to help prevent the clot or thrombus from leaving the target area during the retrieval procedure. Some balloon catheters are designed for neurovasculature applications, these balloon catheters have a small size to track through the smaller vessels of the region and the associated balloons generally need to be quite soft or compliant in order to prevent vessel damage and conform to the shape of the vessel.

Balloon catheters, and especially dual lumen balloon catheters, can be prone to encountering a problem whereby the uninflated balloon inadvertently adheres or sticks to a portion of the catheter (e.g., an inner guidewire lumen or passage) during the inflation of the balloon. This effect is pronounced when a balloon is highly soft or compliant, which is a common feature of balloons used for neurovasculature applications due to the small size of the vessels as well as to enhance flexibility in order to reach these more smaller and more distally located vessels.

This sticking or inadvertent adhering can result in an incomplete inflation of the balloon causing the inflated balloon to have a non-symmetric or non-fully expansile shape within the vessel of the patient being treated and thereby potentially limiting the effectiveness of the treatment procedure. For instance, if a balloon is not completely filled in a flow arrest procedure (e.g., where blood flow is being proximally stopped to help conduct a procedure), blood will still reach the treatment site making the procedure more challenging. In one example, a balloon can be used as part of an aspiration or mechanical clot retrieval procedure, where a balloon is used for proximal flow arrest to help ensure clot or thrombus will not dislodge downstream during the procedure. However, balloon sticking can result in the balloon adopting an incomplete profile, thereby preventing the flow arrest from functioning as intended, and leading to clot or thrombus being dislodged or thrown downstream.

A physician may try to compensate for this issue by overfilling the balloon by applying additional inflation media to try to alleviate the asymmetry or force the balloon to adopt its fully inflated shape, however this can result in too much pressure being applied and cause vessel trauma to the patient, or can result in rupturing of the balloon.

One possible way of getting around this issue is using a stiffer balloon material to reduce the balloon compliance/softness. However, one major drawback is that a stiffer balloon is less compliant and thus less adept and accommodating complex vessel shapes and can cause vessel trauma. Such balloons can also cause complications in certain vessels (e.g., those in the neurovasculature) which are small.

Stiffer materials also affect trackability of a balloon catheter and make it harder to track the balloon catheter around tortuous bends. In one scenario, balloon catheters used in neurovasculature procedures generally need to track through the carotid siphon, which is a U or S-shaped bend in the carotid artery. It would be desirable to access the vasculature of the brain that resides beyond the carotid siphon with a balloon catheter during intravenous procedures such as vessel occlusion, aspiration, flow reversal, clot retrieval, etc. However, it can be difficult to design a balloon catheter that is flexible enough to navigate through tortuous bends (e.g., the carotid siphon), especially when the need for a soft or compliant balloon can cause potential balloon sticking issues.

There is therefore a need for a balloon catheter than can balance at least these needs: flexibility in order to track through tortuous bends, and the ability to use a soft or compliant balloon without the balloon sticking to the catheter.

Many medical procedures utilize a guide catheter as a conduit for smaller catheters (e.g., microcatheters) which are used to access the target region, or to deliver therapeutic devices which are used in a procedure. The guide catheter is larger and stiffer than the smaller catheters delivered through them, and the guide catheter is meant to act as a support structure for the smaller catheters/devices delivered therethrough. The ideal guide catheters would be flexible enough to navigate through tortuous anatomy (e.g., the aforementioned carotid siphon) while also being strong enough to withstand the pulsatile pressure of the anatomy to provide enough structural strength to support deployment of the smaller catheters or devices therethrough.

A balloon guide catheter which includes a balloon that can provide, for example, proximal arrest to augment a therapeutic procedure (e.g., clot retrieval via aspiration or mechanical thrombectomy) and has a large enough passageway to accommodate catheters or additional medical devices would have significant advantages. However, these devices can be challenging to design. For instance, the inclusion of a balloon significantly increases the complexity of a guide catheter since it requires a separate inflation lumen and a balloon which can drastically increase the stiffness of a guide catheter due to the additional parts. This increased stiffness can hurt the trackability of the guide catheter through tortuous anatomy, such as the carotid siphon. Also, there are advantages in utilizing a soft/compliant balloon (e.g., in the neurovasculature space) such as being atraumatic to the vessel wall when inflated, however such a balloon can create stickiness or adhesion issues as discussed above.

Furthermore, these catheters require a balance of flexibility and stiffness/strength. If a balloon guide catheter is too stiff, it will not be able to navigate tortuous anatomy (e.g., the carotid siphon) and thus end up being positioned too far away from the desired destination to provide any benefit (e.g., too far to provide optimal flow arrest for a clot retrieval procedure). This distance can also cause complications where a physician may have to track clot a further distance proximally back into the guide catheter, increasing the risk clot can fragment or dislodge during the retrieval procedure. On the other hand, if a balloon guide catheter is too flexible, it will not be rigid enough to provide support for a smaller catheter or therapeutic devices being delivered through the lumen of the balloon guide catheter and thereby could render a physician unable to complete the procedure.

There is therefore a need for a balloon guide catheter that can balance at least these needs: flexibility in order to track through tortuous bends, the ability to use a soft or compliant balloon without having the balloon stick to the catheter, sufficient structural strength for catheters or devices delivered through a passageway of the balloon guide catheter.

SUMMARY

In one embodiment, a balloon guide catheter is described. The balloon guide catheter utilizes an inner assembly which acts as a passageway for subsequently delivered therapeutic or procedural devices/material (e.g., guidewires, catheters, thrombectomy devices, aspiration/suction, embolic coils, and/or liquid embolic), and an outer assembly which conveys inflation fluid to the balloon. In one embodiment, the balloon guide catheter inner assembly includes a passageway for smaller catheters which are used as a conduit for subsequently delivered therapeutic or procedural devices/material (e.g., thrombectomy devices, aspiration/suction, embolic coils, liquid embolic, embolic meshes, embolic or drug-containing beads, smaller procedural balloon catheters, etc.).

In one embodiment, a balloon guide catheter with a compliant balloon and a mechanism to prevent balloon sticking is described. In one embodiment, the mechanism to prevent balloon sticking can be utilized on balloon catheters of various sizes and functions—not only balloon guide catheters, as a way to prevent this issue.

In one embodiment, the mechanism is one or more grooves located along an external section of an inner assembly of the balloon catheter. In one embodiment, the one or more grooves are longitudinally arranged around the circumference of an inner assembly of a balloon catheter. In one embodiment, the one or more grooves are circumferentially arranged around the circumference of an inner assembly of a balloon catheter. In one embodiment, the one or more grooves are helically arranged around the circumference of an inner assembly of a balloon catheter.

In one embodiment, the mechanism is one or more elevations located along an external section of an inner assembly of the balloon catheter. In one embodiment, the one or more elevations are longitudinally and/or radially arranged. In one embodiment, the one or more elevations are spot elevations or spot projections located in a plurality of locations along the external section of an inner assembly of the balloon catheter.

In one embodiment, the mechanism is one or more depressions located along an external section of an inner assembly of the balloon catheter. In one embodiment, the one or more depressions are longitudinally and/or radially arranged. In one embodiment, the one or more depressions are spot depressions located in a plurality of locations along the external section of an inner assembly of the balloon catheter.

In one embodiment, the mechanism is one or more radially oriented elevations/projections or indentations/depressions/grooves located along an inner assembly of the balloon catheter. In one embodiment, the radially oriented elevations or grooves are created by a coiled element. In one embodiment, the radially oriented elevations or grooves are created by a mesh element.

In one embodiment, a balloon guide catheter utilizes a membrane on a distal portion of the balloon catheter, where the membrane is substantially non-sticky to prevent adhesion of the balloon. In one embodiment, the membrane includes a gapped or cutout section such that a portion of the underlying catheter surface is exposed, where a mechanism to prevent balloon sticking (such as those described above) is utilized along the exposed surface of the catheter to help prevent balloon sticking.

In one embodiment, a balloon guide catheter utilizes a membrane on a distal portion of the balloon catheter, and a purge or escape passage underneath or radially adjacent to the membrane within an inner assembly of the balloon guide catheter, where the purge or escape passage provides an escape for gas from the balloon. In one embodiment, the membrane has pores sized to allow passage of gas but not liquid in order to allow gas to pass through the balloon but prevent passage of liquid (e.g., inflation media such as contrast agent or saline) thereby keeping the balloon inflated.

In one embodiment, a balloon guide catheter for performing procedures around the carotid artery is described. In one embodiment, a balloon guide catheter for performing procedures around the internal carotid artery is discussed. In one embodiment, a balloon guide catheter sized and constructed to navigate through the carotid siphon to perform procedures around the cavernous or clinoid segment of the internal carotid artery of the neurovasculature is discussed. In one embodiment, a balloon guide catheter is sized from about 0.09 inches-0.12 inches outer diameter and has an inner assembly with an inner diameter/passage sized from about 0.08 inches-0.09 inches sized to accommodate catheters sized smaller than the inner diameter of the inner assembly.

In one embodiment, a manufacturing method is described to prevent balloon sticking. In one embodiment, the method comprises placing one or more longitudinal soldering paths along an external surface of a balloon catheter tubular element (e.g., an inner assembly of a balloon catheter). In one embodiment, the method comprises placing one or more coils or meshes around an external surface of a balloon catheter tubular element (e.g., an inner assembly of a balloon catheter)—in one embodiment, the one or more coils or meshes are then removed to leave an imprinted surface. In one embodiment, the method comprises creating one or more ridged interfaces along an external surface of a balloon catheter tubular element (e.g., an inner assembly of a balloon catheter). In one embodiment, the method comprises creating one or more depressed, recessed, or indented interfaces along an external surface of a balloon catheter tubular element (e.g., an inner assembly of a balloon catheter).

In one embodiment, a method of reducing stickiness for a balloon in a balloon catheter is described. In one embodiment, the method comprises creating one or more longitudinal paths utilizing a soldering iron along an external surface of a balloon catheter tubular element (e.g., an inner assembly of a balloon catheter). In one embodiment, the method comprises placing one or more coils wrapped around an external surface of a balloon catheter element (e.g., an inner assembly of a balloon catheter)—in one embodiment, the one or more coils are then removed to leave an imprinted surface. In one embodiment, the method comprises placing one or more meshes around an external surface of a balloon catheter element (e.g., an inner assembly of a balloon catheter)—in one embodiment, the one or more meshes are then removed to leave an imprinted surface. In one embodiment, the method comprises creating one or more ridged interfaces along an external surface of a balloon catheter tubular element (e.g., an inner assembly of a balloon catheter). In one embodiment, the method comprises creating one or more depressed, recessed, or indented interfaces along an external surface of a balloon catheter tubular element (e.g., an inner assembly of a balloon catheter). In one embodiment, the method comprises placing a membrane element circumferentially around a partial external surface of a balloon catheter tubular element (e.g., an inner assembly of a balloon catheter), where the membrane element is substantially non-sticky. In one embodiment, a tubular band element is subsequently placed over a distal portion of the membrane element. In one embodiment, one or more ridged interfaces are placed along an exposed surface of the balloon catheter tubular element (e.g., an inner assembly of the balloon catheter) to create an interface to prevent stickiness or adhesion. In one embodiment, one or more depressed, recessed, or indented interfaces are placed along an exposed section of a balloon catheter tubular element which correspond with a gap in an overlying membrane.

In one embodiment, a method of conducting a vascular procedure is described. In one embodiment, the method comprises providing a balloon catheter (e.g., a balloon guide catheter) with a substantially non-sticky membrane element along a distal portion of the balloon catheter, delivering the balloon catheter to a target treatment site, and delivering an inflation fluid to the balloon to inflate the balloon wherein the substantially non-sticky membrane element prevents the balloon from sticking and thereby promotes proper inflation.

In one embodiment, a method of conducting a vascular procedure is described. In one embodiment, the method comprises providing a balloon catheter (e.g., a balloon guide catheter) with one or more ridged interfaces along a distal portion of the balloon catheter, delivering the balloon catheter to a target treatment site, and delivering an inflation fluid to the balloon to inflate the balloon wherein the ridged interfaces prevent the balloon from sticking and thereby promotes proper inflation.

In one embodiment, a method of conducting a vascular procedure is described. In one embodiment, the method comprises providing a balloon guide catheter and tracking the balloon guide catheter through at least a portion of the carotid siphon, inflating the balloon (e.g., to arrest blood flow), deploying a catheter through and past the balloon guide catheter to a target treatment location to conduct a procedure. In one embodiment, the procedure is aspiration and utilizes suction or vacuum through the catheter which is delivered through the balloon guide catheter. In one embodiment, the procedure is thrombectomy and utilizes a mechanical clot retrieval device delivered through the catheter delivered through the balloon guide catheter. In one embodiment, the procedure is liquid embolic delivery and utilizes a liquid embolic delivered through the catheter which is delivered through the balloon catheter. In one embodiment, the procedure is embolic delivery and utilizes one or more embolic devices (e.g., embolic coils) delivered through the catheter which is delivered through the balloon catheter.

In one embodiment, a method of conducting a vascular procedure is described. In one embodiment, the method comprises providing a balloon guide catheter and tracking the balloon guide catheter through at least a portion of the carotid siphon, inflating the balloon (e.g., to arrest blood flow), and using an inner lumen of the balloon guide catheter for either aspiration or to deploy a device or substance (e.g., mechanical clot retrieval device, liquid embolic, or embolic devices) to a treatment site located in the vicinity of the balloon guide catheter.

In one embodiment, a method of conducting a vascular procedure is described. In one embodiment, the method comprises providing a balloon guide catheter and tracking the balloon guide catheter through at least a portion of the cavernous segment of the internal carotid artery, inflating the balloon (e.g., to arrest blood flow), and using an inner lumen of the balloon guide catheter for either aspiration or to deploy a device or substance (e.g., mechanical clot retrieval device, liquid embolic, or embolic devices) to a treatment site located in the vicinity of the balloon guide catheter.

In one embodiment, a method of conducting a vascular procedure is described. In one embodiment, the method comprises providing a balloon guide catheter and tracking the balloon guide catheter through at least a portion of the internal carotid artery, inflating the balloon (e.g., to arrest blood flow), and using an inner lumen of the balloon guide catheter for either aspiration or to deploy a device or substance (e.g., mechanical clot retrieval device, liquid embolic, or embolic devices) to a treatment site located in the vicinity of the balloon guide catheter. In one embodiment, the balloon guide catheter is tracked through at least one of the cervical (C1) segment, petrous (C2) segment, lacerum (C3) segment, cavernous (C4) segment, or clinoid (C5) segment of the internal carotid artery.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
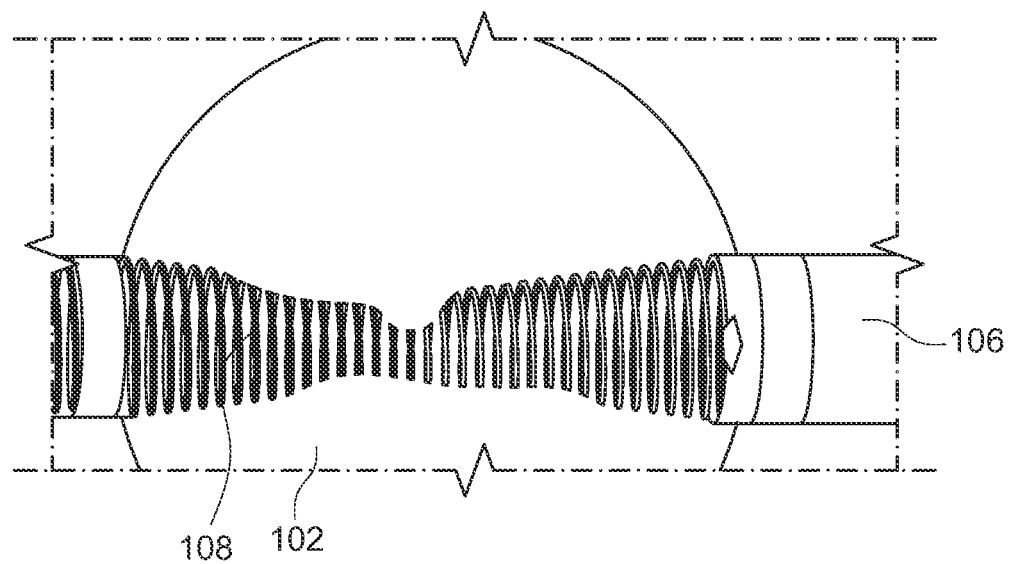
FIG. 1 illustrates a balloon sticking to a portion of a balloon catheter.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Please note, reference may be made to proximal and distal orientations. Proximal refers to the direction toward the outside of the body, toward to the physician conducting the procedure, and away from the treatment location. Distal refers to the direction closer to the vasculature and closer to the target treatment site. In this way, a medical device (e.g., balloon catheter) being pushed distally is being delivered in a direction closer to the treatment site, and a device being pulled in a proximal direction is being withdrawn or being traversed in a direction away from the treatment site.

Balloon catheters, as discussed in the background section above, may have an issue whereby the balloon can stick to a portion of the balloon catheter. This stickiness occurs for various reasons. For instance, where a balloon is soft and compliant, which is a common feature of neurovascular balloons, or balloons used in smaller or more sensitive vasculature regions, this softness and compliance can cause such stickiness or adhesion to a portion of the balloon catheter (e.g., an inner portion positioned radially within the balloon).

The stickiness primarily is an issue when the balloon is in its uninflated shape where a portion of the balloon may stick to a portion of the catheter during this uninflated state. The balloon region continues to adhere to a surface of the catheter during inflation causing the balloon to adopt a non-fully expansile or non-fully inflated shape.

FIG. 1 shows one such severe example where a balloon 102 sticks to a portion of an inner element/guidewire port 106 of a balloon catheter, causing a gap 108 exposing part of inner element 106, such that the balloon is not completely inflated. The particular type of balloon catheter shown is known as a dual-lumen balloon catheter and utilizes one outer element which functions as an inflation lumen used to inflate the balloon and one inner element which functions as a guidewire port. One advantage to a dual lumen system is that a guidewire can be used to advance the balloon catheter to the treatment site utilizing the inner element 106, where the balloon catheter is tracked over the guidewire. The procedure without such a guidewire port requires navigating a guidewire to the treatment site and tracking an overlying sheath or guide catheter over the guidewire, withdrawing the guidewire entirely, then pushing the balloon catheter through the sheath or guide catheter to the treatment site—which is a more laborious and time consuming process.

Figure 2:
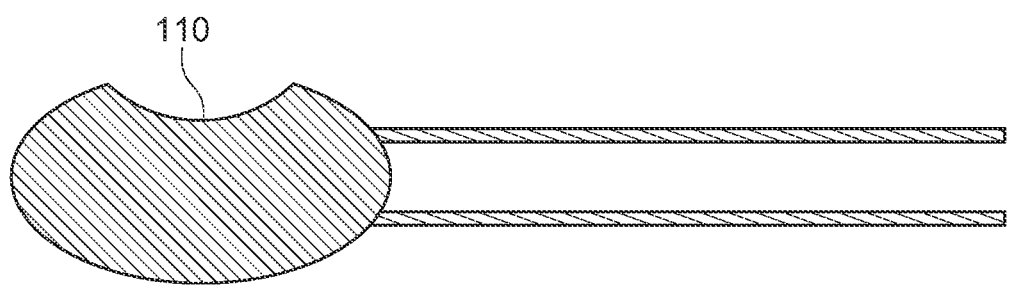
FIG. 2 illustrates a balloon adopting an incomplete profile due to a balloon sticking to a portion of a balloon catheter.

In other examples, a balloon can stick to other portions of the balloon catheter, such as an inflation lumen used to inflate the balloon. This sticking can occur in a dual-lumen device described above (which includes a guidewire port), or in a single-lumen balloon catheter (which utilizes only an outer element/inflation lumen). FIG. 2 shows one example where stickiness of balloon 102 causes the balloon to adopt an incomplete or asymmetrical shape 110.

This stickiness or adhesion of the balloon to a portion of the balloon catheter can cause various complications as discussed in the background section. For instance, the issue can cause a balloon to not adopt a complete profile (e.g., fully circular, elliptical, or ovular profile) thereby reducing the effectiveness of the balloon in the intravascular procedure.

Balloon catheters can be used in various procedures. For instance, they can be used to create flow arrest or create a proximal barrier to augment suction force in an aspiration procedure, create a proximal barrier in a liquid embolic delivery procedure (e.g., to prevent dissipation of the embolic outside of the treatment area), used as a scaffold or backstop in an embolic delivery (e.g., vaso-occlusive coil) procedure. Failure of the balloon to adopt a fully expansile shape can reduce the effectiveness of these procedures since the balloon is prevented from completely sealing against the vessel. For example, in a thrombectomy or aspiration procedure (where thrombectomy utilizes a mechanical clot retrieval device and aspiration utilizes suction or a vacuum to remove a clot), failure of a balloon to adopt a complete/fully expansile shape to occlude a vessel can result in clot being dislodged or can reduce the suction effect of the aspiration procedure. In a vaso-occlusive procedure where the balloon acts as a scaffold, failure of the balloon to adopt a fully expansile shape can cause the vaso-occlusive coils or devices to leave the treatment site (e.g., aneurysm, or a portion of a vessel being occluded) thereby reducing the effectiveness of the procedure or creating a clot risk where the devices migrate elsewhere. In a liquid embolic delivery procedure, failure of the balloon to adopt a fully expansile shape due to stickiness can allow the liquid embolic to reflux away from the treatment site thereby creating a clot or stroke risk in a proximal location, or can allow blood to push the embolic distally thereby treating a distally located clot or stroke risk. Liquid embolics are typically used, for instance, for vessel shutdown or to occlude an arterio-venous malformation (AVM).

Balloon catheters and dual lumen balloon catheters, including such balloon catheters for neurovasculature treatment, are described in U.S. Pat. Nos. 9,884,172 and 10,786,659 and both are incorporated by reference herein in their entirety.

Physicians may respond to the balloon-sticking issue by trying to overinflate the balloon in order to force additional inflation media into the balloon to force a fully expansile shape. However, such over-inflation can cause the balloon to rupture, can drastically increase balloon pressure against the vessel wall causing rupture over time, or may be traumatic to the vessel.

The embodiments presented herein solve this problem by addressing the issue of balloon stickiness or adhesion.

Figure 3:
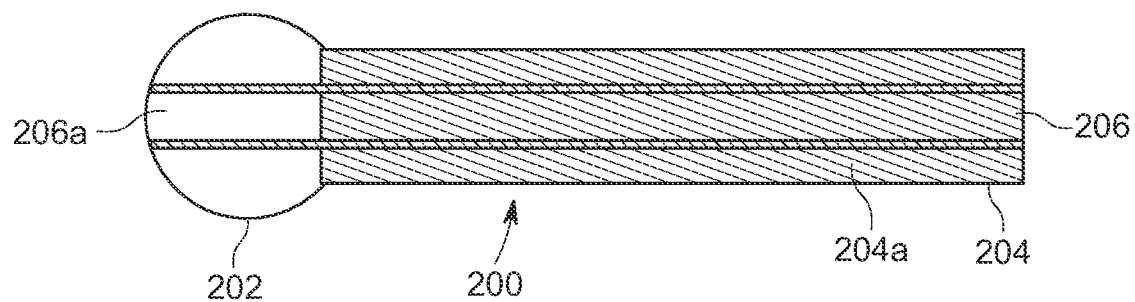
FIG. 3 illustrates a balloon catheter (e.g., a balloon guide catheter), according to one embodiment.

FIG. 3 shows a dual lumen balloon catheter 200, according to one embodiment, which includes an inflatable balloon 202, an outer assembly 204 which contains a passage 204*a* therein that acts as a conduit for inflation fluid to inflate the balloon, and an inner assembly 206 containing its own passage therein. In one example, liquid inflation media such as contrast agent or saline is used to inflate balloon 202, where the inflation media is delivered through a passage 204a of outer assembly 204.

Each of the inner 206 and outer 204 assemblies are tubular (e.g., each a tubular assembly) and are concentrically arranged such that the inner assembly 206 is concentrically located within the outer assembly 204. Each of the inner 206 and outer 204 assemblies can be considered a tubular assembly (e.g., an inner tubular assembly 206 and an outer tubular assembly 204). Each of the inner 206 and outer 204 assemblies contain a passage, channel, or elongated lumen 206a, 204a spanning an entire length of each. The outer assembly 204 has a lumen 204a formed therein which is partially occupied by the inner assembly 206 which is located through an entirety of the outer assembly 204 and spans or extends distally beyond the outer assembly 204, as shown in FIG. 3.

Inner assembly 206 and outer assembly 204 can each be composed of various combinations of polymeric layers and metallic reinforcement layers (e.g., metallic coils or braids). In one example, each assembly 204, 206 utilizes a plurality of polymeric layers. In one example, each assembly 204, 206 utilizes a plurality of polymeric layers and at least one of the assemblies 204, 206 can further utilize at least one metallic reinforcement layer to provide additional structural strength. Different sections of each of the inner assembly 206 and outer assembly 204 can be configured with different combinations of structural layers, for instance a more proximal section can utilize stronger materials (e.g., more rigid polymers) while a more distal section can utilize more flexible materials (e.g., softer polymers).

Figure 4:
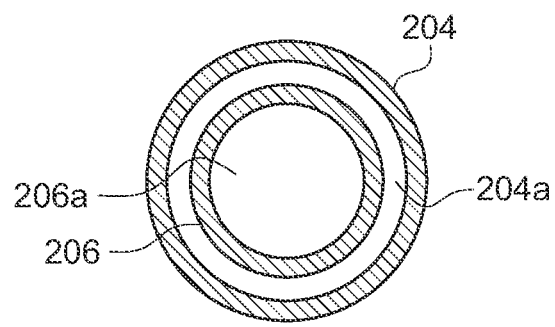
FIG. 4 illustrates a cross-sectional representation of the balloon catheter of FIG. 3, according to one embodiment.

A cross-sectional perspective of the balloon catheter showing the inner 206 and outer 204 assemblies is shown in more detail in FIG. 4. Inner assembly 206 includes a lumen 206a, which in one embodiment functions as a passageway for a catheter where the dual lumen balloon 200 functions as a balloon guide catheter. Outer assembly 204 includes an inflation lumen 204a which is formed in the space between an inner wall of the outer assembly 204 and an outer wall of the inflation lumen 204a, as this represents the open space between inner assembly 206 and outer assembly 204.

A proximal end of the balloon catheter 200 includes a hemostatic or y-shaped adapter (not shown) with two ports (each port forming branches of the y-type shape), where a first port is in communication with the inflation lumen 204a to convey inflation fluid (e.g., saline or contrast agent) distally to the balloon 202 while a second port is in communication with the inner lumen or passage 206a in order to convey material therethrough (e.g., a catheter containing a medical device or a catheter which acts as a throughway for aspiration).

A distal portion of inner assembly 206 utilizes a mechanism to prevent the balloon from sticking to an external surface of the inner assembly 206. As shown in FIG. 3, inner assembly 206 spans an entire length of balloon catheter 200 including an entire length of balloon 202. The distal portion of balloon catheter 200 is shown in more detail in FIG. 5 where the approximate location of mechanism 208 is shown.

Figure 5:
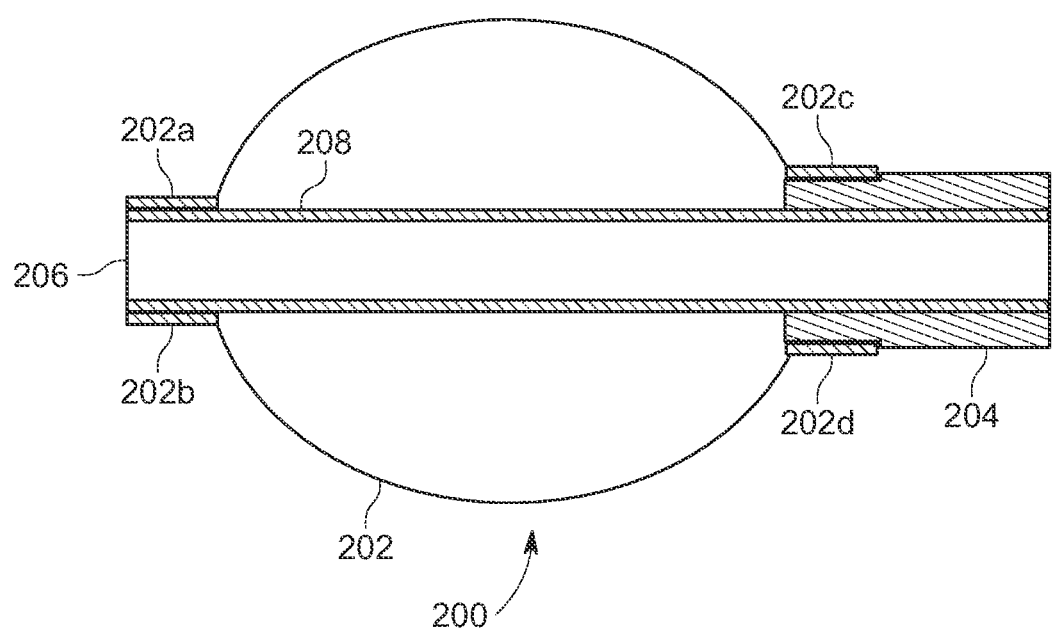
FIG. 5 illustrates a distal section of the balloon catheter of FIG. 3, according to one embodiment.

Balloon 202 is bonded proximally to outer assembly 204 at positions 202c, 202d—this bonding is either to an external surface of outer assembly 204 (as shown in FIG. 5), or can be along an inner wall of outer assembly 204. Balloon 202 is bonded distally to inner assembly 206 at positions 202a, 202b along an outer/external surface of inner assembly 206. As shown in the Figures, balloon 202 does not inflate at these bonding positions 202a-202d since the balloon is attached to the inner 206 or outer 204 assembly (e.g., via adhesive) at these locations. In other words, the portion of balloon 202 between these bonding positions inflates or deflates, while balloon 202 is fixed and does not inflate at bonding positions 202a-202d.

Figure 6A:
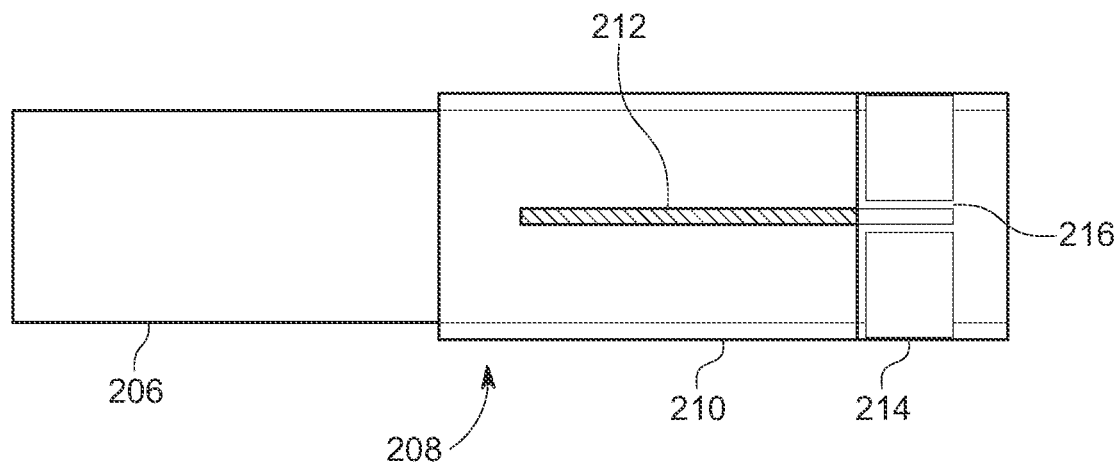
FIGS. 6a-6b illustrate a distal section of a balloon catheter incorporating a non-sticking mechanism, according to one embodiment.
Figure 6B:
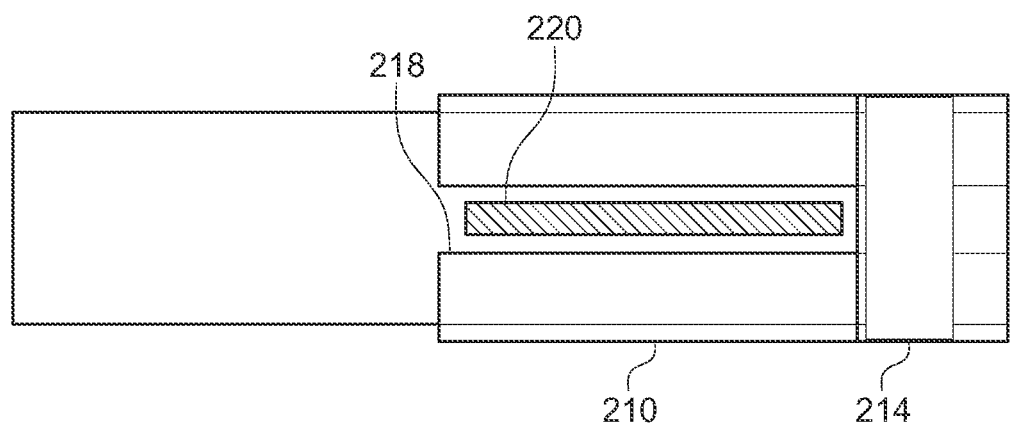

Region 208 of balloon catheter 200 is shown in more detail in FIGS. 6a-6b. Please note the left to right view is considered proximal to distal, so the right side is considered the distal end of the balloon catheter. A membrane 210 overlies an external surface of inner assembly 206. An elongated purge passage or channel 212 is positioned within a structural layer or wall of inner assembly 206 and is further positioned under membrane 210. A marker band 216 is distally positioned and includes a gap 216 to accommodate the channel 212.

Membrane 210 is positioned over and around the inner assembly 206. In one embodiment, membrane 210 is a sheet of material, which, in a curled state where the ends of the sheet meet, has a smaller (or similar) overall circumference than the circumference of the inner assembly 206. As a result, the ends of the sheet will not mate with one another when positioned over the inner assembly 206. This results in a gap between the two ends of the membrane 210 when membrane 210 is positioned over inner assembly 206. This gap will result in an exposed section 218 of inner assembly 206 which is not covered by membrane 210. In one embodiment, membrane 210 is placed over the inner assembly 206 and then a portion of the membrane 210 is cut or removed to create an exposed section 218 of inner assembly 206. Membrane 210 is bonded to inner assembly 206, for example via adhesive or by the mechanism of a marker band 216 which in one example is positioned over a distal portion of membrane 210.

Since membrane 210 covers a partial circumferential portion of inner assembly 206, membrane 210 can also be considered, for example, an overlying layer (e.g., one that covers a partial circumferential portion of inner assembly 206), overlying element, partial circumferential layer/element, a radially outward layer/element, external layer/element.

An outer or external surface of inner assembly 206 has an exposed section 218 (meaning not covered by membrane 210) and one or more elements 220 are positioned on this exposed section 218. Elements 220 are configured as roughened sections, projecting surfaces, or recessed surfaces which serve to create a non-flat interface to prevent balloon sticking when the balloon is in its deflated state. The created interface prevents the balloon from sticking or adhering to the surface of inner assembly 206 (e.g., along exposed section 218).

FIG. 6a shows one view (e.g., a top view) of region 208 of balloon catheter 200, where along this top view there is an elongated purge passage or channel 212 positioned within the inner assembly 206 and under membrane 210. FIG. 6b shows another view (e.g., a bottom view) of region 208, where along this bottom view there is an exposed region 218 and one or more elements 220 along this exposed region 218, which will be discussed in more detail later. In one example, channel 212 and elements 220 are diametrically opposed 180 degrees from each other. In another example, they are offset from each other by a certain number of circumferential degrees (e.g., between 5-180 degrees or 90-180 degrees).

In one embodiment, elements 220 comprise one or more indented, grooved, or recessed regions projecting into the surface of inner assembly 206. These indentations can be made in a variety of ways, for instance a wire or mandrel can be positioned on the surface of inner assembly 206 and then heated (e.g., via an iron such as a soldering iron) along its length to imprint into the surface of inner assembly 206. The wire or mandrel is then withdrawn to leave the imprinted shape which forms an indented, grooved, or recessed surface (e.g., as shown in FIG. 6d). Where a plurality of indented surfaces are created, the technique can utilize a plurality of wires spread around the exposed region 218 of inner assembly 206. In one embodiment, the indented, grooved, or recessed regions are created by a heating element which is passed along a surface of inner assembly 206 thereby melting into the surface of inner assembly 206 and leaving an indented surface along the length of the path of the heating element. In one embodiment, the process of creating the indented region will move material out from the indented region to the area adjacent to the indent, thereby leaving an indentation, and a raised region immediately adjacent to the indentation where the moved material migrates.

Figure 6C:
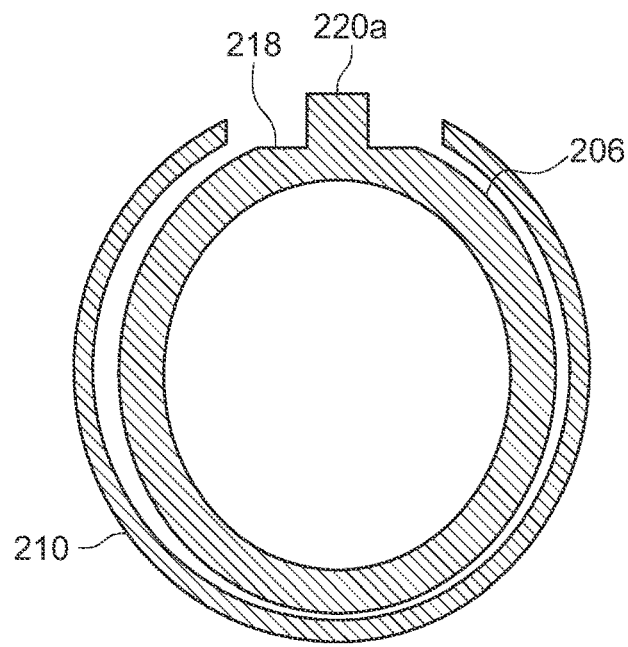
FIG. 6c illustrates a cross-sectional representation of a balloon catheter utilizing a projecting surface, according to one embodiment.
Figure 6D:
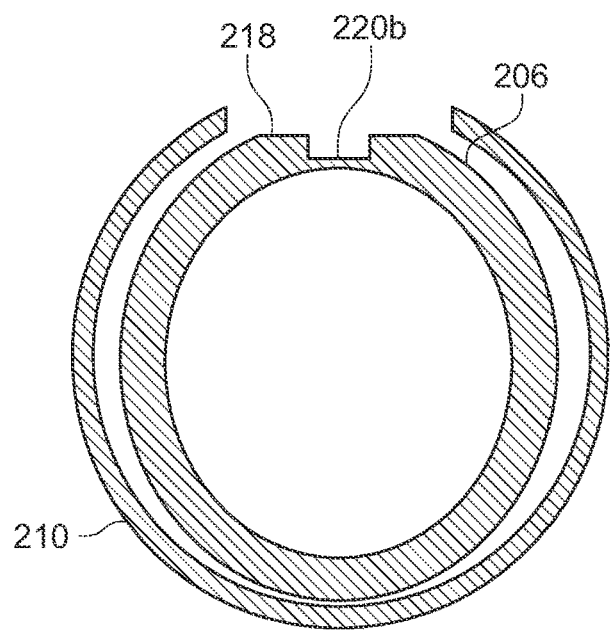
FIG. 6d illustrates a cross-sectional of a balloon catheter utilizing an indented surface, according to one embodiment.

In one embodiment, elements 220 comprise one or more projecting regions projecting outwardly from the surface of inner assembly 206, (e.g., as shown in FIG. 6c). The projecting regions can be formed, for instance, by utilizing flux from a soldering iron in an additive capacity to create a projecting surface along the path of the soldering iron.

In one embodiment, the indented or projecting regions form one or more continuous lines. In one embodiment, the indented or projecting regions are helical in nature (e.g., extending in a helical or coil-like path along a surface of inner assembly 206). In one embodiment, the indented or projecting regions are spotted or point-like in nature where the projecting or indented surfaces are applied to a localized point along a surface of inner assembly 206.

In some embodiments, various additive technologies such as deposition, 3d printing, additive elements (e.g., elements glued or physically attached to an external surface of inner assembly 206) can be used to create projecting surfaces. In some embodiments, technologies such as deposition, 3d printing, and reducing technologies (e.g., utilizing a pin element or a rigid element to remove external sections of inner assembly 206) can be used to create indented or recessed surfaces along inner assembly 206.

FIG. 6c shows a cross-sectional representation where membrane 210 is positioned partially around/over a portion of inner assembly 206 leaving an exposed section 218, and further utilizing a projecting surface 220a along inner assembly 206. Please note more than one projecting surface 220a can be utilized along exposed section 218. Furthermore, the projections 220a can be combined with recessed, indented, or depressed surfaces (shown in FIG. 6d) where, for instance, a projecting surface can be positioned next to or adjacent an indented, recessed, or depressed surface—as shown in FIGS. 6e and 6f.

Figure 6E:
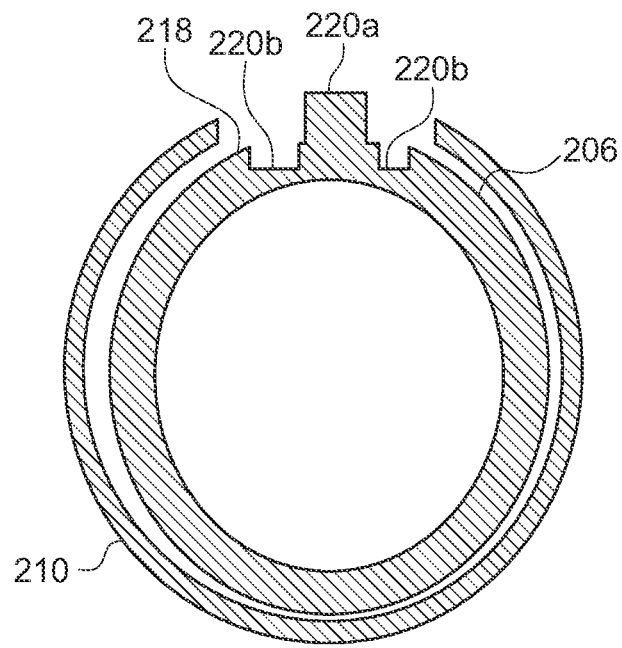
FIG. 6e illustrates a cross-sectional of a balloon catheter utilizing a projecting surface and an indented surface, according to one embodiment.
Figure 6F:
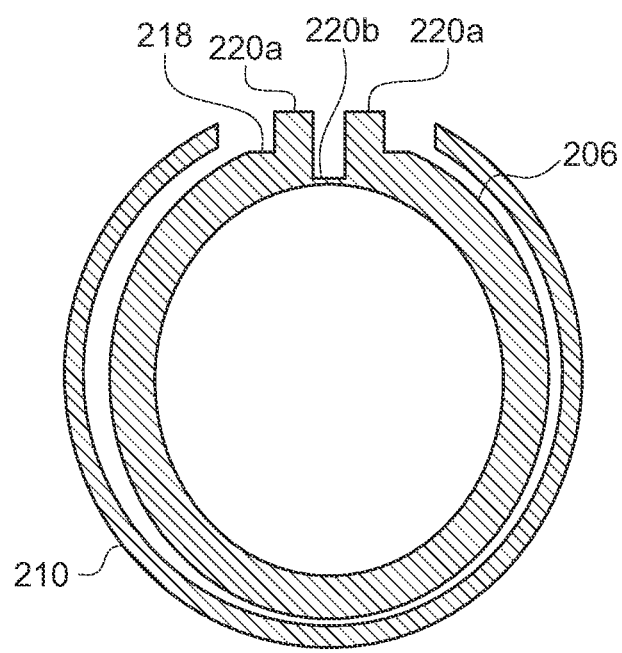
FIG. 6f illustrates a cross-sectional of a balloon catheter utilizing a projecting surface and an indented surface, according to one embodiment.

FIGS. 6c-6e help to illustrate how the projecting 220a or indented 220b surfaces help to prevent balloon sticking. Without the inclusion of these elements 220a or 220b, an entire exposed section 218 of inner assembly 206 is potentially available to contact a portion of balloon 220, creating an extended region of potential adhesion. However, with the inclusion of elements 220a or 220b, a roughened or uneven surface is created, reducing the total surface area available to contact balloon 200 in its uninflated state and thereby reducing the risk of balloon sticking or adhesion. For example, where a raised surface 220a is used, balloon 200 in its noninflated state may only contact the "top" part of the raised surface 200a and is less likely to contact the adjoining regions as the balloon "lifts" in relation to the rest of the exposed surface 218. Where an indented surface 220b is used, balloon 200 in its noninflated state may only contact a portion of the "lifted" surface next to the indented surface 220b, but not the indented surface itself 220b. In other words, the inclusion of elements 220a or 220b reduces the overall surface area available to contact balloon 200 when uninflated, thereby reducing the risk of adhesion as balloon 200 inflates.

In one example, a plurality of projections (e.g., 2, 3, 4, 5, 6, 7, 8, 9, 10, 11, or 12) are formed in circumferentially equidistant spaces around the periphery of a distal section of inner assembly 206. In one embodiment, the projections are only applied along an exposed section 218 of inner assembly 206. One such advantage to this configuration is that the manufacturing step of creating the projections only needs to be applied to the exposed section 218 of the assembly 206 (or, in other words, the portion of the inner assembly 206 not covered by membrane 210), rather than the entire circumference of inner assembly 206, thereby easing the manufacturing and assembling process. In another embodiment, these projections are applied all along the circumference of a distal section of inner assembly 206, and then membrane 210 is placed over the inner assembly 206 where the grooves are then exposed only along the exposed section 218.

FIG. 6d shows a cross-sectional representation where membrane 210 is positioned partially around/over a portion of inner assembly 206 leaving an exposed section 218, and further utilizing a recessed, indented, or depressed surface 220b along inner assembly 206. Surface 220b can also be considered as a groove. Please note more than one recessed, indented, or depressed surface 220b can be utilized along exposed section 218. Furthermore, the recessed, indented, or depressed surfaces 220b can be combined with projecting surfaces (shown in FIG. 6c) where, for instance, a projecting surface can be positioned next to or adjacent an indented or recessed surface.

In one example, a plurality of grooves (e.g., 2, 3, 4, 5, 6, 7, 8, 9, 10, 11, or 12) are formed in circumferentially equidistant spaces around the periphery of a distal section of inner assembly 206. In one embodiment, these grooves are only applied along an exposed section 218 of inner assembly 206. One such advantage to this configuration is that the manufacturing step of creating the grooves only needs to be applied to the exposed section 218 of the inner assembly 206 (or, in other words, the portion of the inner assembly 206 not covered by membrane 210), rather than the entire circumference of inner assembly 206, thereby easing the manufacturing and assembling process. In another embodiment, these grooves are applied all along the circumference of a distal section of inner assembly 206, and then membrane 210 is placed over the inner assembly 206 where the grooves are then exposed only along the exposed section 218.

In one embodiment, one or more longitudinal grooves/indented surfaces are formed along an outer surface of inner assembly 206 by placing a metal mandrel or wire 70 along a surface of inner assembly 206. The mandrel or wire is then heated and pressed into the exterior surface of inner assembly 206 using a soldering iron. The soldering iron is moved down the length of the mandrel or wire to ensure even heating and depression into the inner assembly 206. Once a groove is formed, the mandrel is removed and relocated to make another longitudinal groove on another circumferential section of inner assembly 206 (if more than one groove is desired).

Other embodiments of elements 220 can utilize one or more spot divots (i.e., indented, depressed, or recessed surfaces) or one or more spot projections created, for instance, by placing a soldering iron or piercing element (e.g., a pin) over various sections of inner assembly 206 to create a number of different surfaces or textures across the exposed portion 218 of inner assembly 206.

Please note the various embodiments presented toward creating surface features on a surface of a catheter (e.g., grooves, indentations, ridges, projections, depressions, recessions, etc.) are used in order to create a non-smooth surface to prevent balloon adhesion or sticking. As such, these elements (e.g., grooves, indentations, ridges, projections, depressions, recessions, etc.) can be considered as surface features, roughened regions, a surface with a variable shape or profile, or a substantially non-smooth surface in order to accomplish this goal. Furthermore, where these elements project from the surface of a catheter (e.g., an inner assembly 206) they can be considered as surface projections, surface ridges, etc. Where these elements extend into are indented into the surface of a catheter (e.g., an inner assembly 206) they can be considered as surface grooves, surface indentations, surface depressions, surface recessions, etc. In a manner that will be explained herein, the surface features reduce a contact area between an inner portion of balloon 200 and the inner assembly 206 (e.g., an exposed portion 218 of inner assembly 206) thereby reducing or eliminating the risk of balloon sticking or adhesion.

In one embodiment, membrane 210 is non-sticky or substantially non-sticky so that the balloon cannot stick to the membrane in its deflated state. In one example, membrane 210 is composed of ePTFE. In this manner, balloon 202 is prevented from sticking to the surface of the inner assembly 206 by both the non-stickiness of membrane 210 and the elements 220 preventing adhesion or sticking along gap section 218 which is not covered by membrane 210. One factor influencing balloon stickiness is the relative softness of the material contacting balloon 202, so membrane 210 is preferably composed of a material that is harder than that of the balloon 202.

In one embodiment, membrane 210 spans of a length of about 1-50, 5-30, 5-15, 5-10, or about 7-8 millimeters from the distal tip of the inner assembly 206. In one example, elements 220 (e.g., projections 220a, indentations 220b) span a length of about 1-50, 5-30, 5-15, 10-15, or about 13 millimeters from the distal tip of the inner assembly 206. In these embodiments, membrane 210 and elements 220 do not span an entire length of balloon 202. One reason is that the balloon stickiness is generally more of an issue at the distal region of the balloon. In order to augment flexibility of the distal region of the catheter, the inner assembly 206 (as will be discussed later) utilizes a soft polymeric element at a distal tip region which creates or contributes to the potential stickiness issue. Furthermore, the more medial portion of the balloon 202 (e.g., further away from bonding locations 202a-202d shown in FIG. 5) may not necessarily rest directly against or adjacent the inner assembly 206 surface when the balloon is in a deflated state, meaning the balloon stickiness or adhesion is more of a factor along the distal region of balloon 202.

Other embodiments may utilize membrane 210 and/or elements 220 along a surface of inner assembly 206 corresponding to substantially an entire length of balloon 202, or a large portion of balloon 202. Where membrane 210 and/or elements 220 are positioned along substantially an entire length of balloon 202, this would correspond to a substantial entire length of a the portion of inner assembly 206 which is positioned distal of outer assembly 204 since balloon 202 is proximally connected to outer assembly 204 and distally connected to inner assembly 206—as shown in FIG. 5.

Membrane 210 serves another important function in that it includes a number of pores (e.g., a large number of small pores to produce a porous profile) and the pores allow the membrane to allow passage of gas into the underlying channel 212; in this way channel 212 can be considered as a purge channel or a de-airing channel. The pores of membrane 210 are sized large enough to allow passage of gas into the underlying channel, but are too small to allow passage of liquid. In this way, the membrane allows passage of gas but retains liquid and this allows a user to de-air or de-gas the balloon prior to an intravascular procedure. To prepare the balloon for the intravascular procedure, the user would send inflation media (e.g., saline or contrast agent) into the balloon, where the inflation media would displace any retained gas or air which is then pushed out of the membrane through the pores and into channel 212. Once the inflation media starts to inflate the balloon, the user would know that all the air or gas has been purged from the balloon and the user can then pull proximally against a syringe plunger or use a vacuum system to draw the inflation media back from balloon 202 to deflate the balloon.

Channel 212 runs all the way to the distal tip of the balloon catheter 200 (i.e. exiting the distal tip of inner assembly 206) and, as such, the channel 212 allows the gas or air to be expelled distally of the balloon catheter 200/balloon 202. In another example, channel 212 ends at a location proximal of the distal tip but the section of the catheter inner assembly 206 utilizing channel 212 is thicker than a distal extremity of the inner assembly 206 that is devoid of this channel (e.g., a small, recessed distal tip section is positioned distal of the section utilizing channel 212) and in this way, the channel 212 still expels the gas or air from inner assembly 206.

In one example, membrane 210 is an ePTFE layer with a thickness of about 0.0006"-0.0007" and a pore size of about 0.4-0.6 microns. Pores of this size range will prevent passage of liquid (e.g., saline or contrast agent) but allow passage of air/gas. The membrane polymer can be treated in a number of different ways to impart pores of an appropriate size to create the membrane. In one preferred embodiment, the polymer is heat treated in order to make the polymer stretchable, the polymer is then stretched to create several pores therein, then reheated to lock in the particular stretched shape. In another embodiment, a chemical is utilized and the chemical eats through the polymer in order to create the membrane. In another embodiment, an e-spun process can be used to create a spider-web like structure with appropriately sized pores. In another embodiment, the membrane is a porous foam material.

Membrane 210 (e.g., ePTFE), as discussed above, is substantially non-sticky and so will not adhere to the balloon material. Balloon 202 is preferably formed of a soft material, which is useful for neurovasculature applications. In one embodiment, balloon 202 is formed of Polyblend 45A or other polymeric elastomeric material. The balloon 18 may have an outer diameter of up to approximately 15 millimeters and a length in the range of 5 to 50 millimeters and, preferably a length in the range of 10 to 20 millimeters.

Two soft surfaces will tend to adhere or stick to each other. Balloon catheter 200 includes a softer distal tip segment utilizing a soft polymeric material (e.g., a low-density polyethylene, or a low-durometer Pebax) at the distal tip segment of inner assembly 206, which is positioned on the outer surface of inner assembly 206 and below membrane 210. The softer distal interface helps enhance flexibility along the distal portion of balloon catheter 200. Membrane 210 (utilizing, for example, ePTFE) is at least slightly harder than the underlying soft polymeric material of the inner assembly 206, thereby reducing the stickiness between the membrane 210 and the balloon 202 due to the increased relative hardness of the membrane 210. Furthermore, the pores of membrane 210 create a number of small uneven elements across the surface of membrane 210, creating an uneven surface, further helping to contribute to the non-stickiness of the membrane 210.

An additional advantage to the use of a softer distal tip segment on inner assembly 206 (e.g., through a low-density polyethylene, or a low-durometer Pebax distal element) is that since the distal tip of inner assembly represents the distal end or distal extremity of balloon catheter 200, the softer the tip is the less potential damage the balloon catheter 200 can make to the vessel. In this way, a softer distal tip is less traumatic to the vessel.

Figure 7:
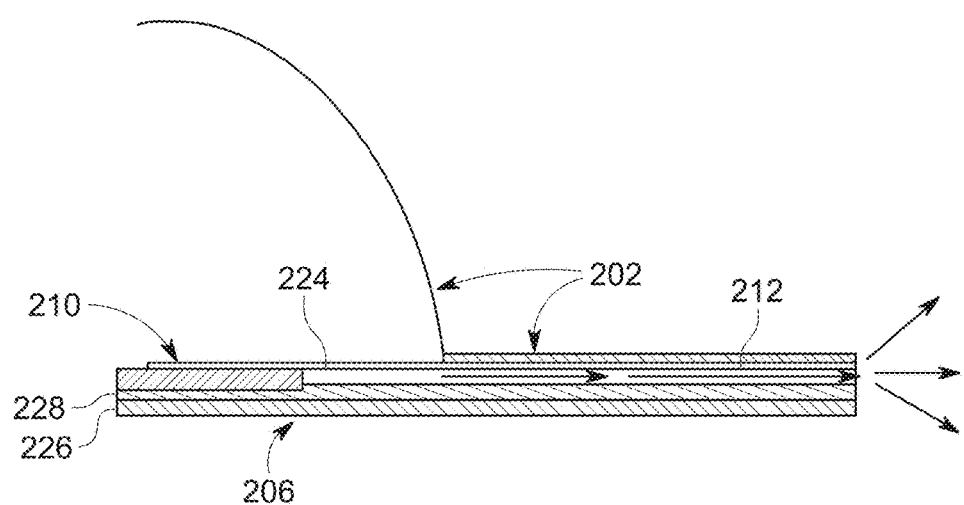
FIG. 7 illustrates a distal section of balloon catheter incorporating a membrane and a purge passage, according to one embodiment.

FIG. 7 shows another view of the distal section of balloon catheter 200, and illustrates the membrane 210 and purge passage 212 in more detail, where the right side shows the more distal portion of balloon catheter 200. Inner assembly 206 is composed of a polymeric inner liner 226 (e.g., PTFE) and an overlying structural polymeric layer 228. Membrane 210 is positioned over the polymeric layer 228 and the outer surface of membrane 210 faces the inner surface of balloon 202. In this manner, when the balloon 202 is uninflated it rests against the membrane 210 and when the balloon 202 is inflated it adopts the configuration shown in FIG. 7. A distal section of the balloon 202 is bonded to a distal portion of membrane 210 is shown in FIG. 7, where the balloon is proximally and distally bonded as discussed earlier (e.g., proximally bonded to a distal section of outer assembly 204 and distally bonded to a distal section of inner assembly 206).

The elongated purge passage or channel 212 is created by placing a thin mandrel rod within polymer layer 228 during the assembly process. After assembly, the mandrel rod is then removed leaving the elongated passage 212 shown in FIG. 7. Membrane 210 is positioned over polymer layer 228 (including elongated passage 212). Membrane 210, as discussed earlier, envelopes a partial circumferential exterior of polymer layer 228 of inner assembly 206 and leaves a circumferential gap corresponding with an exposed section 218 of inner assembly 206, as shown in FIG. 6b-6d.

In one embodiment, polymer layer 228 is a relatively soft material (e.g., a low-density polyethylene or a low-durometer Pebax), whereby the addition of the harder membrane 210 (e.g., where membrane 210 utilizes a higher durometer polymer or a higher density ePTFE molecular profile) over the polymer layer 228 helps mitigate any sticking between the extremely compliant/soft balloon 202 and the inner assembly 206.

In one embodiment, polymer layer 228 is a harder/more rigid polymer (e.g., a high-density polyethylene or a high-durometer Pebax) and then an additional soft material layer (e.g., a low density polyethylene or a low-durometer Pebax) is positioned over this layer along a distal segment of the inner assembly 206 (e.g., along the segment of inner assembly 206 underlying membrane 210) in order to increase flexibility along the distal region of the inner assembly 206 to augment trackability of the balloon catheter 200.

FIG. 7 also shows a purge port 224 which acts as the conduit between the balloon and the purge passage or channel 212. Port 224 functions as the conduit for gas escaping the balloon as it proceeds through the pores of membrane 210 and then into and through the purge passage 212.

Earlier presented embodiments, (e.g., shown in FIG. 6b) discussed the utilization of elements 220 specifically within an exposed section of inner assembly 206 not covered by membrane 210 in order to provide a mechanism to prevent balloon stickiness or adhesion in the section not covered by membrane 210. The elements 220, as discussed earlier, can take on a variety of configurations including raised or projection surfaces, indentations/grooves/depressed/recessed surfaces, etc. Other embodiments of these elements 220 can utilize different configurations in order to create a roughened, unsmooth, or uneven shape in order to resist balloon adhesion to the surface. In one embodiment, a coil (e.g., a metallic coil shape) is positioned over the outer surface of inner assembly 206, and later removed to imprint a coil shape. The coil leaves a linearly oriented circular imprint or helical grooves over where it was positioned. This creates a roughened and imprinted or recessed shape in area where the coil was formerly located, and a raised or projected surface in the adjacent area (which is raised relative to the area where the coil was located). In other embodiments, a braid can be used in order to create a more complex imprinted surface shape. Due to the inclusion of the overlying membrane 210 (where only a portion 218 of the inner assembly 206 is exposed), the elements 220 are located all along the exposed section 218 of inner assembly 206, as well as under membrane 21—but elements 220 are only exposed and therefore provide a functional benefit of reducing adhesion or stickiness along the exposed surface 218.

In one embodiment, a wire is wrapped around an outside surface of inner assembly 206, and then heated. A tube of heat-shrink tubing is then placed around the wiring and heat is applied to cause the tubing to shrink onto the wire, thereby pressing the heated wire into the outside of the inner tubular element to form a number of grooves. Once cooled, the shrink wrap is then off of the inner assembly 206 and the wire is then removed, leaving a number of grooves. The membrane 210 is then positioned over a portion of the inner assembly 206, leaving an exposed grooved surface positioned over the exposed gap region 218.

In one embodiment, a braided mesh tube could be used in a similar manner to form a different pattern. The distal end of the inner assembly 206 is placed within a braided tube, the tube is stretched to reduce the diameter around the inner assembly 206, and the tube is then heated to a temperature that softens the catheter material. A separate heat shrink tube can then be applied to press the braided tube into the catheter, making a patterned impression on the outside surface of inner assembly 206. Membrane 210 is then positioned over a portion of inner assembly 206, as described above.

Other embodiments can utilize membrane 210 placed around an entire periphery of a distal section of inner assembly 206 (e.g., whereby there is no exposed region 218 of inner assembly 206). The non-stickiness of the membrane 210 against the inner surface of balloon 202 will prevent balloon adhesion.

Other embodiments can completely avoid the use of membrane 210. Instead, the longitudinal grooves/indentations, longitudinal projections, spot divots, spot projections, helical grooves, helical projections, etc. as discussed in the embodiments presented earlier are placed circumferentially along an exterior portion of inner assembly 206. One advantage to a system whereby no membrane is used and instead one or more longitudinal grooves or indentations located circumferentially along inner assembly 206 is that where these grooves or indentations span a significant length of balloon 202, they can be used to convey inflation fluid (e.g., contrast or agent) distally to the balloon 202 to help create a more even or consistent inflation process. The grooves or indentations (e.g., 220b) leave a channeled surface allowing passage of the inflation fluid, where the inflation fluid is pushed distally as more inflation fluid is added to the balloon thereby ensuring a more even inflation profile especially along a distal section of the balloon. In one example, during a prepping procedure to remove air from the balloon, inflation media is initially conveyed through the balloon to push air out of the balloon and into the purge passage 212 (described earlier, and shown in FIG. 6*a*). The indentations would also create a channel for air to be pushed distally to the membrane and purge passage 212 of the balloon catheter 200 to be purged from the balloon.

Figure 6G:
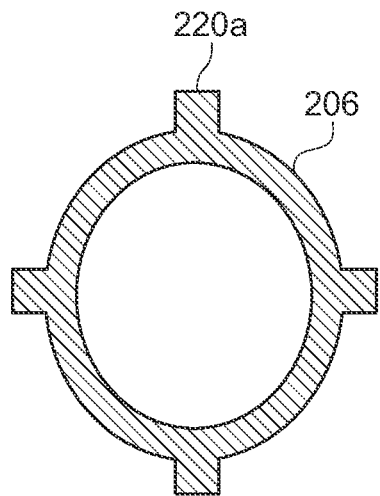
FIG. 6g illustrates a cross-sectional of a balloon catheter utilizing a plurality of projecting surfaces, according to one embodiment.
Figure 6H:
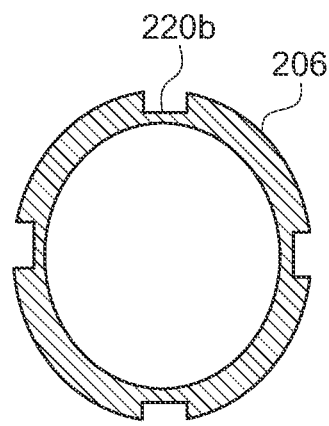
FIG. 6h illustrates a cross-sectional of a balloon catheter utilizing a plurality of indented surfaces, according to one embodiment.
Figure 6I:
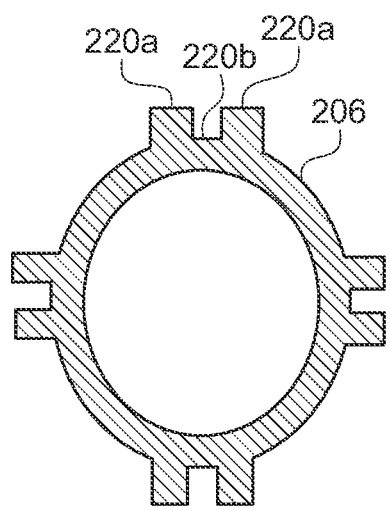
FIG. 6i illustrates a cross-sectional of a balloon catheter utilizing a plurality of projecting surfaces and a plurality of indented surfaces, according to one embodiment.
Figure 6J:
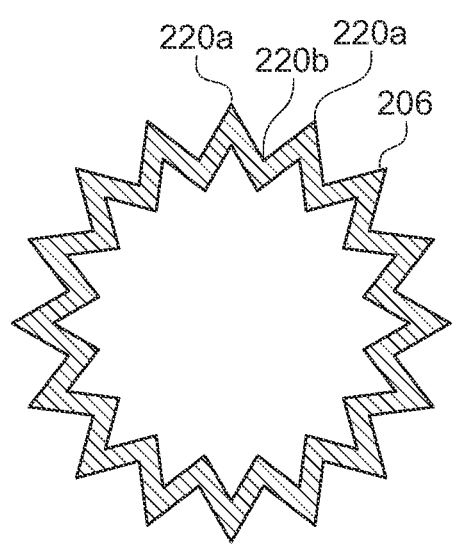
FIG. 6j illustrates a cross-sectional of a balloon catheter utilizing a plurality of projecting surfaces and a plurality of indented surfaces, according to one embodiment.
Figure 6K:
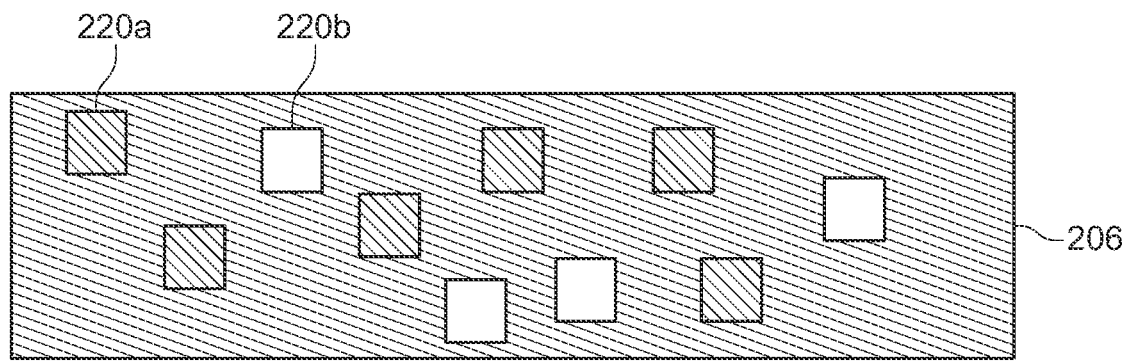
FIG. 6k illustrates a cross-sectional of a balloon catheter utilizing a plurality of spot projecting surfaces and a plurality of spot indented surfaces, according to one embodiment.
Figure 6L:
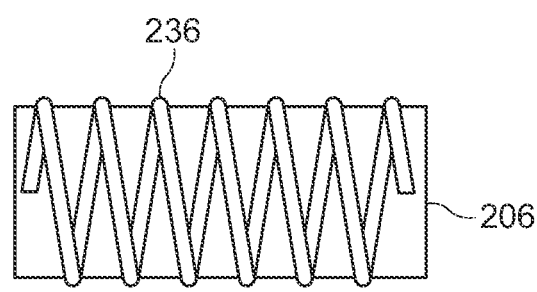
FIG. 6*l* illustrates a cross-sectional of a balloon catheter utilizing a coiled element used to create a helical grooved indentation, according to one embodiment.

These concepts are shown in FIGS. 6*g*-6*i*, where no membrane is used and different combinations of projections 220*a* and indentations 220*b* are used. Though rectilinear shapes are shown, in some embodiments (including those utilizing membrane 210), the shapes can be rounded or pointed in nature. More pointed shapes 220*a*, 220*b* are shown in FIG. 6*j*. FIG. 6*k* shows a plurality of spot projections 220*a* and spot divots/indentations 220*b* randomly spread across the surface of inner assembly 206. FIG. 6*l* shows a configuration described earlier where a coil 236 is initially placed on a surface of inner assembly 206, the coil 236 is subsequently removed leaving a helical groove/indentation along the surface of inner assembly 206 mirroring the placement of coil 236.

Note, that even where a membrane 200 is used (and thereby, projecting regions 220*a* or indentations 220*b* have a functional benefit along exposed section 218 of inner assembly 206), indentations 220*b* would still have a benefit in providing a channel for air passage during the air purge step, and providing a channel for distal inflation fluid passage along the exposed section 218 of inner assembly 206, and therefore would also provide such a procedural benefit.

The previous embodiments have discussed various mechanisms to reduce balloon sticking in a balloon catheter. In some embodiments, these mechanisms are used as part of a balloon guide catheter.

The background section discussed the various difficulties with designing a balloon guide catheter as well as the advantages to such a system. Currently, balloon catheters are delivered through an overlying guide catheter. When used for neurovasculature procedures or procedures at or near the carotid artery, the guide catheter should ideally be able to navigate the carotid siphon which is a highly tortuous U or S-shaped bend of the more distal section of the carotid artery, and specifically the internal carotid artery.

The carotid siphon provides access to the neurovasculature. Failure of a guide catheter to have sufficient flexibility to navigate the carotid siphon can result in the guide catheter being unable to navigate this bend, leaving a smaller procedural catheter (e.g., a microcatheter, distal-access catheter, or a procedural balloon catheter) unshielded in attempting navigate through to the target treatment location.

The guide catheter is crucial as it is larger and more rigid and therefore provides support for the smaller procedural catheter, however it must be sufficiently flexible to navigate through tortuous anatomy such as the carotid siphon. While having sufficient flexibility to navigate the carotid siphon, the guide catheter must also be sufficiently strong to not buckle under the tortuous and pulsatile nature of the vasculature and must be strong enough to act as a support for the smaller catheters delivered through the guide catheter.

The use of a balloon guide catheter would be particularly advantageous as a guide catheter having a balloon could be used as a supporting structure and access throughway for a smaller procedural catheter (e.g., a microcatheter, distal-access catheter, or a smaller procedural balloon catheter—where the smaller catheter delivered through the balloon guide is then used to deliver medical devices, therapeutic substances, or as a conduit for aspiration/suction). The balloon guide can then be used to provide flow arrest proximal of the procedure site where after deployment of the smaller procedural catheter though a lumen of the balloon catheter, the balloon is then utilized to provide, for example, proximal flow arrest to limit blood flow to the treatment area.

A balloon guide catheter would also be particularly advantageous for particular procedures. For instance, for an aspiration procedure or a thrombectomy procedure used to retrieve clot/thrombus, the balloon guide catheter can be used to provide a proximal seal (via the balloon) to limit blood flow to the treatment site as the clot/thrombus retrieval procedure takes place. The inner passage of a balloon guide catheter is used as a throughway for a smaller catheter (e.g., microcatheter or distal-access catheter) which is a conduit for aspiration or a thrombectomy device which conducts the procedure.

Figure 8:
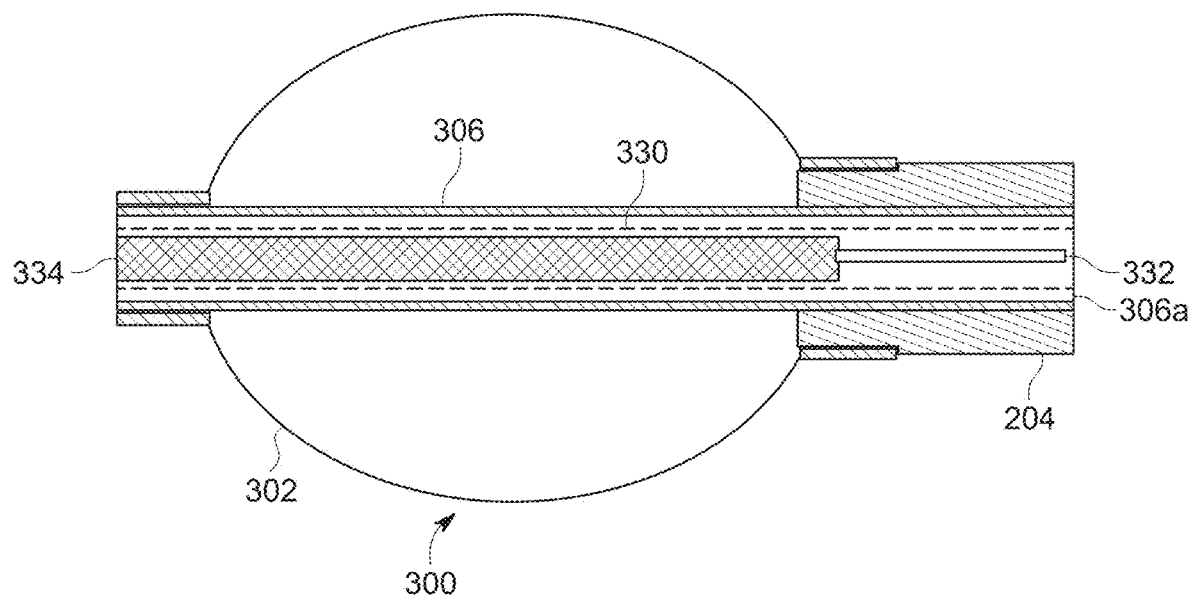
FIG. 8 illustrates a balloon guide catheter used as a conduit for a smaller procedural catheter, according to one embodiment.

FIG. 8 shows an example where a balloon guide catheter 300 is used to deliver a mechanical thrombectomy device. As will be appreciated by those of skill in the art, the attributes of the embodiments discussed above can be applied to other systems, including, for example, a balloon guide catheter as disclosed herein.

The passage 306*a* of inner assembly 306 is used as a throughway for a smaller procedural catheter 330 (e.g., a microcatheter in the example of FIG. 8) where the procedural catheter 330 (e.g., microcatheter) contains a thrombectomy device 334. In one example, thrombectomy device 334 is a stent-like device also known as a stentriever which is configured like a stent but used for clot capture, and has an open distal end sized to capture clot or thrombus and a closed proximal end connected to a delivery pusher 332 used to deliver the device to the treatment site (i.e., pushing the thrombectomy device 334 out of microcatheter 330). Balloon 302 can either be inflated during the delivery procedure (as shown in FIG. 8), or it can be inflated after the procedural catheter 330 (e.g., microcatheter) and thrombectomy device 334 are delivered to the treatment site to conduct the clot/thrombus retrieval procedure. In one example, the thrombectomy device comprises a plurality of engaging members used to engage the clot or thrombus, such as the device described in U.S. Pat. No. 9,211,132, which is incorporated by reference herein in its entirety.

In one exemplary embodiment, the procedural catheter 330 acts as a conduit for aspiration whereby an aspiration/vacuum source (e.g., vacuum pump) is linked proximally to the procedural catheter 330 to suction clot/thrombus at a treatment location. Balloon guide catheter 300 is navigated through (and optionally past) at least a portion of the carotid siphon to access the region of the neurovasculature. A procedural catheter 330 (e.g., a microcatheter, distal access catheter, or smaller balloon catheter) is then navigated through an inner passage 306*a* of the balloon guide catheter 300 and to the target treatment location. Balloon 302 of the balloon guide catheter 300 is inflated in order to provide proximal flow arrest and limit blood flow to the target treatment site, and then the procedural catheter 330 is used to conduct an aspiration procedure whereby clot or thrombus is suctioned or aspirated into the procedural catheter 330.

The example provided above is used illustratively, as a variety of devices can be delivered through procedural catheter 330, such as vaso-occlusive coils, liquid embolics, embolic or drug-containing beads/microspheres, embolic meshes stents. In one example, procedural catheter 330 is a smaller balloon catheter where the balloon guide 330 can provide proximal flow arrest near the carotid siphon while the smaller balloon catheter delivered through the balloon guide catheter 300 provides flow arrest closer to the treatment location.

Several of the previous examples have discussed the use of proximal flow arrest via balloon 302 of a balloon guide catheter 300. This is useful for several reasons. The inflation of balloon 302 fills or occludes the region around the catheter 300 with the inflated balloon, acting as a flow barrier for blood flowing distally. The procedural catheter 330 at the treatment location while the balloon guide catheter 300 is deployed proximal to the treatment location (e.g., in the vicinity of the carotid artery, for instance at or around the carotid siphon), where the balloon 302 of balloon guide catheter 300, once inflated, helps limit blood flow to the target treatment location. This limited blood flow is useful for preventing, for example, shifting of the clot/thrombus during a retrieval procedure (e.g., where clot or thrombus can fragment during an aspiration or retrieval by a mechanical thrombectomy device) to a more down-stream location. In this way, flow arrest helps prevent clot or thrombus from dislodging or migrating further downstream during a retrieval procedure.

Flow arrest through inflation of balloon 302 of a balloon guide catheter 300 is also useful in other procedures. For instance, the balloon guide catheter 300 itself can be used for aspiration, where inner assembly 306 functions as a conduit for aspiration/vacuum where suction is delivered through the inner assembly passage 306a. This procedure can be used, for instance, where the clot or thrombus is positioned proximal or a bit distal of the carotid siphon, as opposed to the more distal and smaller neurovasculature regions (e.g., where the balloon guide catheter 300 can easily be tracked). In this manner, balloon 302 will provide an immediate proximal flow barrier for the aspiration procedure, where the aspiration procedure takes place utilizing the balloon guide catheter 300 itself.

In other procedures where a procedural catheter 330 is delivered through the balloon guide catheter 300 for other purposes (e.g., vaso-occlusive coil or mesh delivery, liquid embolic delivery, embolic/drug containing bead delivery, etc.), balloon 302 provides proximal flow arrest proximal of the treatment site, helping to prevent blood from pushing the therapeutic substances delivered through the procedural catheter 330 away during the delivery procedure. In this manner, the balloon 302 is optionally inflated for the duration of the procedure, where after the therapeutic substances are deployed through procedural catheter 330, the procedural catheter 330 is retracted into the balloon guide catheter 330, balloon 302 of balloon guide catheter 300 is deflated, and the balloon guide catheter 300 is withdrawn from its location.

Necessary properties of a properly functioning balloon guide catheter were described earlier. These include sufficient flexibility to get through the more tortuous anatomy of the vasculature (e.g., the carotid siphon) while also being strong enough to act as a throughway for the smaller catheters (e.g., microcatheters and distal access catheters) being delivered through the balloon guide catheter.

The additional mechanisms required in a balloon catheter (e.g., inflation lumen, balloon) can vastly increase the stiffness of a balloon guide catheter in comparison to a typical guide catheter, creating a unique design challenge in that a balloon guide catheter may be considerably more stiff that a traditional guide catheter due to the inclusion of the material required for a balloon and for inflation of the balloon. In order to decrease the stiffness and increase the flexibility of a balloon guide catheter, certain features can be utilized. For instance, the inclusion of a softer distal polymer segment of a balloon catheter, such as low-density polyethylene or a low-durometer Pebax as discussed in the embodiments presented earlier. However, the inclusion of the softer system can lead to balloon sticking (e.g., since balloon 302 itself is soft). Therefore, the use of mechanisms described in the embodiments above (e.g., where some configurations are shown in FIGS. 6a-6c) to mitigate the issue of balloon sticking (e.g., through the use of membrane 210, elements 220 positioned along the surface of inner assembly 206) are helpful in creating a usable balloon guide catheter.

In one embodiment, balloon guide catheter 300 is sized from about 0.09 inches-0.12 inches outer diameter and has an inner assembly with an inner diameter (meaning the size of passage 306a of inner assembly 306) sized from about 0.08 inches-0.09 inches sized to accommodate catheters sized smaller than the inner diameter of the inner assembly. Please note the sized indicated are useful for particular target vasculature regions (e.g., navigating the carotid siphon region of the vasculature), but the balloon guide catheter can be sized up or down as needed.

The passage 306a of inner assembly 306 of balloon guide catheter 300 has particular functionality in being used as a conduit for procedural catheters 330 (e.g., smaller catheters such as microcatheters or distal access catheters) which can be used to deliver subsequent items (e.g., medical devices, aspiration, therapeutic substances, etc.). In one example, the procedural catheter 330 is a distal access catheter which is then used as a conduit for a smaller catheter (e.g., a microcatheter) which is then used for the delivery of subsequent items (e.g. medical devices, aspiration, therapeutic substances, etc.). In one example, the distal access catheter itself is used for the delivery of subsequent items (e.g. medical devices, aspiration, therapeutic substances, etc.).

Passage 306a of inner assembly 306 of balloon guide catheter 300, in one example, is initially used as a conduit for a guidewire which is a small access wire used to navigate the guide catheter to the vicinity of the treatment location (e.g., the carotid siphon region). In one example, the balloon guide catheter is anchored at or distally beyond the carotid siphon, the guidewire is navigated past this region to the treatment location, and the procedural catheter 330 is navigated over the guidewire to the treatment location. The guidewire is then removed.

In various embodiments, methods of use or procedural methods are described. In one embodiment, a method comprises a user tracking a balloon guide catheter through at least a portion of a carotid siphon region of the vasculature, deploying a procedural catheter (e.g., a microcatheter or a distal access catheter) through an inner assembly or inner passage of the balloon guide catheter and distal of the balloon guide catheter to a treatment site, inflating a balloon on the balloon guide catheter to provide flow arrest proximal to the target treatment site, and conducting a procedure utilizing the procedural catheter. In various embodiments, the procedure can be aspiration, mechanical thrombectomy, or embolic delivery where the procedural catheter is the conduit for the aspiration, mechanical thrombectomy device, or embolic material. The mechanical thrombectomy device can be a clot retrieval device or a stentriever. The embolic material can comprise liquid embolic, embolic meshes, or embolic/vaso-occlusive coils. In one embodiment, the method comprises further tracking a guidewire through an inner passage of the balloon guide catheter and using the guidewire to navigate the balloon guide catheter to a particular location, and then using the guidewire to navigate the procedural catheter to a treatment location (e.g., where the treatment location is distal to the balloon guide catheter location). The guidewire is retracted once the target treatment location is reached.

In one embodiment, a method comprises navigating or tracking a balloon guide catheter through at least a portion of a carotid siphon region of the vasculature, inflating a balloon on the balloon guide catheter, and using an inner passage of the balloon guide catheter to conduct a vascular procedure. In one embodiment, the vascular procedure is aspirating a clot or thrombus where aspiration, suction, or a vacuum is delivered through the inner passage of the balloon guide catheter.

A balloon guide catheter, as discussed above, has particular utility in navigating tortuous bends such as the carotid siphon of the internal carotid artery. The carotid siphon leads to the neurovasculature arteries and therefore is a bend or tortuous section that needs to be navigated to access the neurovasculature. The internal carotid artery is made of several segments. In a proximal (away from the neurovasculature) to distal (toward the neurovasculature) direction, these segments comprise the cervical segment (C1), petrous segment (C2), lacerum segment (C3), cavernous segment (C4), clinoid segment (C5), ophthalmic segment (C6), and C7 (communicating segment). The carotid siphon is located along a distal section of the cavernous segment (C4), where the clinoid segment (C5) is distally positioned relative to the carotid siphon.

In discussing a balloon guide catheter having the ability to navigate the carotid siphon, this means being able to navigate through the cavernous segment to the carotid siphon region, therefore the ability to navigate at least through the cavernous segment or C4 segment of the internal carotid artery. Depending on the size of the vessels and the associated flexibility of the balloon guide catheter (e.g., various embodiments discussed ways to augment flexibility), a user may be able to track the balloon guide catheter to more distal regions including, for example the clinoid C5 segment or even potentially the ophthalmic C6 segment and communicating segment C7. In other words, a balloon guide catheter can potentially be used in more distal regions of the vasculature. Similarly, the embodiments presented herein can be sized up or sized down as needed to create a balloon guide catheter or balloon catheter that can operate in larger arties or smaller arteries.

In some examples, balloon guide catheter 300 can be used procedurally within other segments of the internal carotid artery such as the C1-C4 segments.

Methods of use, as discussed earlier and herein, can be understood as navigating various sections of the vasculature such as the internal carotid artery, as well as navigating the relevant segments of the internal carotid artery to position a balloon guide catheter. In this way, when a user positions a balloon guide catheter or a balloon catheter through at least a portion of the carotid siphon, this entails navigating the catheter through the C1-C3 segments and at least a significant portion of the cavernous C4 segment since the carotid siphon is located along this C4 segment.

In one embodiment, a method of conducting a vascular procedure comprises navigating a balloon guide catheter through the internal carotid artery through the cavernous segment of the internal carotid artery through at least a portion of the carotid siphon, inflating the balloon, and conducting a vascular procedure utilizing an inner passage of the balloon guide catheter. In one embodiment, the procedure further comprises passing a procedural catheter through the inner passage of the balloon guide catheter and performing a procedure (e.g., device delivery, or aspiration) utilizing the procedural catheter. In one embodiment, the procedure comprises utilizing the inner passage of the balloon guide catheter for aspiration in the vicinity of the balloon guide catheter. In one embodiment, the steps described herein can be utilized with a balloon catheter. In one embodiment, the balloon guide catheter or balloon catheter utilizes elements to reduce balloon stickiness (e.g., a membrane 210 and/or elements 220). In one embodiment, a method as described herein is utilized to conduct a procedure along another segment of the internal carotid artery (e.g., the C1, C2, or C3, C5, C6, or C7 segments). Where the procedure is conducting distally beyond the cavernous C4 segment (e.g., the C5-C7 segments), the procedure comprises navigating the catheter entirely through the carotid siphon. In some embodiments, the methods as described herein can be used to navigate a balloon guide catheter or a balloon catheter through any tortuous section of the vasculature, where the catheter can be sized and purposed (e.g., with the sufficient level of strength and flexibility) accordingly.

Note, given the carotid siphon leads to the neurovasculature, there is particular utility in having a balloon guide catheter navigating the carotid siphon and being able to provide flow arrest (via the inflated balloon) while a passageway of the balloon guide catheter is use as a conduit for a procedural catheter (e.g., a microcatheter or distal access catheter) used to perform a procedure. In one example, the procedural catheter (e.g., distal access catheter) is used to perform aspiration at a more distal region in the neurovasculature (meaning distal of the location of the balloon guide catheter), where the inflated balloon of the balloon guide catheter aids in reducing blood flow to the target region thereby helping perform the procedure. In one example, the passage of the balloon guide catheter itself is used to perform an aspiration procedure in the vicinity of the balloon guide catheter. This latter example is useful, for instance, where clot or thrombus is located in a region the balloon guide catheter is capable of navigating (e.g., the C1-C5, C3-C5, or C4-C5 segments of the internal carotid artery).

Please note, though the description has primarily focused on ways to reduce stickiness and how these concepts can be used in order to create a useable balloon guide catheters, these concepts can also be used on other balloon catheters (e.g., not only balloon guide catheters) in order to create a more usable balloon catheter. As such, the balloon catheters discussed can be sized larger or smaller as needed incorporating the ideas presented herein to be used in a variety of scenarios.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:
1. A balloon catheter comprising:
an outer assembly having an inflation lumen;
an inner assembly spanning a length of the outer assembly and extending distally past the outer assembly;

a balloon proximally connected to the outer assembly and distally connected to the inner assembly; the balloon in communication with the inflation lumen of the outer assembly; and a layer affixed to a distal portion of the inner assembly, the layer positioned partially around a circumference of the distal portion of the inner assembly so as to define a slot such that the inner assembly has an exposed portion underlying the slot that is not covered by the layer;

wherein the exposed portion of the inner assembly includes one or more surface projections positioned within the slot.

2. The balloon catheter of claim 1, wherein the one or more surface projections extend longitudinally along the exposed portion of the inner assembly.

3. The balloon catheter of claim 2, wherein the one or more surface projections extend longitudinally beyond the exposed portion of the inner assembly.

4. The balloon catheter of claim 2, wherein the one or more surface projections extend longitudinally beyond the exposed portion of the inner assembly.

5. The balloon catheter of claim 1, wherein the one or more surface projections comprise a plurality of surface projections.

6. The balloon catheter of claim 1, wherein the one or more surface projections extend in a circumferential manner along the exposed portion of the inner assembly.

7. The balloon catheter of claim 6, wherein the one or more surface projections are formed from a coil or mesh imprinted into a surface of the inner assembly.

8. The balloon catheter of claim 1, wherein the exposed portion of the inner assembly includes one or more surface indentations.

9. The balloon catheter of claim 8, wherein the one or more surface projections are adjacent to the one or more surface indentations.

10. The balloon catheter of claim 1, wherein the layer is a membrane.

11. The balloon catheter of claim 10, wherein the membrane is substantially non-sticky.

12. The balloon catheter of claim 10, wherein the membrane is composed of ePTFE.

13. The balloon catheter of claim 10, wherein the membrane contains a plurality of pores sized to allow passage of gas but prevent passage of liquid.

14. The balloon catheter of claim 10 wherein the membrane is positioned radially external of an elongated purge passage, and the elongated purge passage is positioned within the inner assembly and configured to expel gas from the balloon.

15. The balloon catheter of claim 1, wherein the balloon catheter is a balloon guide catheter and where the inner assembly has a passageway sized to accommodate a procedural catheter.

16. The balloon catheter of claim 1, wherein the one or more surface projections extend longitudinally along the exposed portion of the inner assembly.

17. The balloon catheter of claim 1, wherein the one or more surface projections comprise a plurality of surface indentations.

18. The balloon catheter of claim 1, wherein the one or more surface projections extend in a circumferential manner along the exposed portion of the inner assembly.

19. A balloon catheter comprising:

an outer assembly having an inflation lumen;

an inner assembly spanning a length of the outer assembly and extending distally past the outer assembly;

a balloon proximally connected to the outer assembly and distally connected to the inner assembly; the balloon in communication with the inflation lumen of the outer assembly; and a layer affixed to a distal portion of the inner assembly, the layer positioned partially around a circumference of the distal portion of the inner assembly so as to define a slot such that the inner assembly has an exposed portion underlying the slot that is not covered by the layer;

wherein the exposed portion of the inner assembly includes one or more surface indentations underlying the slot, wherein the one or more surface indentations are indented into a surface of the inner assembly.

20. A balloon guide catheter comprising:

an outer assembly having an inflation lumen;

an inner assembly spanning a length of the outer assembly and extending distally past the outer assembly; the inner assembly having a passageway allowing passage of a procedural catheter;

a layer affixed to and positioned partially around a circumference of the inner assembly so as to define a slot; and a balloon proximally connected to the outer assembly and distally connected to the inner assembly; the balloon in communication with the inflation lumen of the outer assembly;

wherein an external surface of the inner assembly includes at least one of: one or more surface projections positioned within the slot or one or more surface indentations underlying the slot, wherein the one or more surface indentations extend into a surface of the inner assembly.

* * * * *